United States Patent [19]

Kiamil

[11] Patent Number: 5,697,961

[45] Date of Patent: Dec. 16, 1997

[54] COMPRESS FOR USE IN THE COLD AND/OR HOT TREATMENT OF AN INJURY

[75] Inventor: Sinan Kiamil, Hotch Warren, United Kingdom

[73] Assignee: Scholl PLC, Windsor, United Kingdom

[21] Appl. No.: 163,913

[22] Filed: Dec. 7, 1993

[30] Foreign Application Priority Data

Oct. 8, 1993 [GB] United Kingdom ............ 9320747

[51] Int. Cl.$^6$ ............................................. A61F 7/00
[52] U.S. Cl. .................. 607/108; 607/114; 126/204; 62/530
[58] Field of Search ............... 607/105–114; 62/530; 165/46; 383/901; 126/204, 207

[56] References Cited

U.S. PATENT DOCUMENTS

| | | | |
|---|---|---|---|
| 3,736,769 | 6/1973 | Peterson | 607/112 |
| 3,780,537 | 12/1973 | Spencer | 62/530 |
| 3,871,376 | 3/1975 | Kozak | 607/114 |
| 4,404,820 | 9/1983 | Romaine | 62/530 |
| 4,527,565 | 7/1985 | Ellis | 128/402 |
| 4,671,267 | 6/1987 | Stout | 604/291 |
| 4,865,012 | 9/1989 | Kelley | 126/204 |
| 4,908,248 | 3/1990 | Nakashima et al. | 428/355 |
| 4,920,964 | 5/1990 | Francis, Jr. | 607/114 |
| 5,150,707 | 9/1992 | Anderson | 607/114 |
| 5,163,425 | 11/1992 | Nambu et al. | 607/116 |
| 5,391,198 | 2/1995 | Cheney, III et al. | 607/114 |
| 5,447,531 | 9/1995 | Wood | 607/108 |

FOREIGN PATENT DOCUMENTS

| | | |
|---|---|---|
| 0 123 949 | 3/1984 | European Pat. Off. . |
| 55-068366 | 5/1980 | Japan . |
| 59-053411 | 3/1984 | Japan . |
| 59-110617 | 6/1984 | Japan . |
| 61-168350 | 7/1986 | Japan . |
| 63-006080 | 1/1988 | Japan . |
| 64002647 | 1/1989 | Japan . |
| 1270867 | 10/1989 | Japan . |
| 4092662 | 3/1992 | Japan . |
| 1 404 171 | 8/1975 | United Kingdom . |
| 2 160 425 | 12/1985 | United Kingdom . |
| 2 218 908 | 11/1989 | United Kingdom . |
| WO 90/01913 | 3/1990 | WIPO . |

*Primary Examiner*—Robert L. Nasser
*Attorney, Agent, or Firm*—Sheridan Ross P.C.

[57] ABSTRACT

A compress suitable for use in hot and cold treatments of an animal or human body part is described, such compress comprising a flexible container containing a formulation comprising an aqueous solution and discrete particles of a crosslinked, water-absorbing polymer. In one embodiment, the compress is contained in a sealed plastic bag. The formulation used in the compress can further comprise an anti-freeze agent, a salt compound, a glycol compound or mixtures thereof. The crosslinked, water-absorbing polymer in one embodiment is polyacrylamide or sodium polyacrylate.

12 Claims, 3 Drawing Sheets

COMPRESS FOR USE IN THE COLD AND/OR HOT TREATMENT OF AN INJURY

The present invention relates to Hot/Cold Compress area of an animal or human body, and particularly, but not exclusively, for use in the treatment of sports injuries.

FIELD OF THE INVENTION

Background of the Invention

Compresses have been found to be a useful form of applying cold and hot to parts of a human or animal body. The application of cold or hot temperatures is a useful adjunctive aid in the treatment of sports injuries, such as muscle strain, and the treatment has been found to control the symptoms, facilitate healing, and thus allow the patient to rehabilitate more effectively. Basically, a cold compress used in such treatment acts as a vasoconstrictor, and has the effect of decreasing tissue metabolism, inflammatory response, pain and muscle spasm in the region of its application. A hot compress has been found to act as a vasodilator, increase tissue metabolism, local circulation and tissue extensibility, and decrease pain in the region of its application.

Various cold compresses are available. These compresses generally take the form of a filled pack, which is placed in a freezer to freeze or cool its contents, and then pressed against the affected area. Common disadvantages with such known cold compresses is that the temperature of the product starts to rise immediately and noticeably on removal from the freezer and when cold they lack sufficient conformability to the part of the body to which they are applied. Many compresses are also inefficient to manufacture or use. The following are examples of publications in this field:

U.K. patent application No. 2,160,425 discloses a cold compress whose content is mainly water to which glycerol is added so that the contents do not freeze at 0° C. The contents may also contain a thickening agent in the form of a linear, non-crosslinked polymer.

U.K. patent No. 1,404,171 discloses a cold compress which has at least one layer of a cold storing material which may be a gel, such as a polyacrylamide gel layer. Irradiation will be necessary to form the polyacrylamide into the gel layer. This has the disadvantage that only relatively thin layers of this gel can be formed, as the radiation will not penetrate relatively thicker layers, and thus, if a thick layer of the cooling material is required, the compress must be built up of several layers as taught in the patent.

U.S. Pat. No. 4,404,820 discloses a cold compress which is again in the form of a solid gel layer. In this patent, the layer is formed from polyvinyl alcohol which covers a support pad of polyurethane foam.

European patent publication No. 0 123 949 discloses a compress comprising a gel formed by freezing an aqueous solution of polyvinyl alcohol. An anti-freeze agent may be added to the solution prior to freezing and this is disclosed as improving the mechanical strength of the gel. The gel may be used in the form of small pieces, and these pieces may be formed either by casting the aqueous solution of the polyvinyl alcohol into a plurality of small moulds, or by moulding a large mass which is then cut into a plurality of small pieces. The pieces of gel are then put into a flexible envelope, which is cooled. This is obviously a very inefficient way of forming small pieces of gel.

U.S. Pat. No. 4,527,565 discloses a compress which uses a water-based gel product which includes an anti-freeze so that it does not freeze.

Despite these various disclosures, many people with, or treating, injuries find the most effective and efficient treatment is obtained by simply using a bag of frozen peas as a cold compress.

SUMMARY OF THE INVENTION

The preset invention seeks to overcome the above-mentioned disadvantages and provide a compress which has good conformability to its site of application when cold, which maintains its cold temperature for a period of time, and is efficient to manufacture.

The present invention also seeks to provide a compress which has the advantage of being suitable for use in hot as well as cold treatment. The above publications do not disclose a compress for hot treatment let alone a compress which is suitable for both types of treatment, and indeed it will be recognised that at least some of the products are not suitable for use in hot treatment, e.g. the gel disclosed in European patent publication No 0 123 949 will turn into a solution upon heating. If such a product is then frozen, a large frozen mass of polymer will result.

The present invention also seeks to provide a compress which is easily re-useable simply by re-cooling or re-heating the compress.

Thus according to one aspect of the present invention there is provided a compress suitable for use in the cold and hot treatment of a part of the human or animal body comprising: a flexible, closed container containing: an aqueous solution, and a crosslinked, water-absorbing polymer.

Crosslinked water absorbing polymers are known per se. Dispersion in such polymers is resisted because the crosslinks restrict the movement and complete separation of the polymer chains, but the polymer does swell when solvent molecules diffuse into the network and cause the chain to expand. Preferred examples of such polymers for use in the present invention include crosslinked polyacrylamide and sodium polyacrylate, which are commercially available from Allied Colloids under the trade names ALCOSORB and SALSORB respectively. These polymers take the form of white granules when dry, which swell on absorbing water and other aqueous solutions to form discrete particles.

The conformability of the product of the present invention to its site of application is largely due to the ability of the polymer to form these discrete hydrated particles which move over each other to enable the compress to be moulded to the required shape. However, some other factors can affect the conformability of the product and these can be readily varied by a skilled worker to achieve the desired result in any given circumstance. These other factors will now be described by way of example below.

The conformability of the product is further determined by the degree of hydration of the polymer. In practice, as the water content of the polymer is increased, there is an increased tendency for the swollen polymer particles to stick together when frozen to form a solid lump, which can be likened to a block of ice. In most cases, the solid block can be broken down in a similar way to ice; however, the size of the broken pieces can be large and it may be difficult to break these down to the desired size. The reason for the formation of a large block from the higher water content polymer particles is that such particles are very soft, flexible and fluid and they can come close together to expel all the air in between them. This increases the surface area of contact between particles, which then freeze in the form of a lump. On the other hand, if the polymer is partially hydrated, the polymer particles are soft but resilient and hence exist as individual particles with minimum contact between them. When the partially hydrated particles are frozen, even if the particles form a large lump, this breaks down relatively easily into individual particles and becomes free flowing.

Similarly, it has been found that, if the discrete, partially hydrated particles are compressed, then the contact area between particles is increased and air between them expelled. If the product is then placed in a freezer in the compressed state, a block of frozen particles again forms. However, even in this form, the block is easier to break down than the block formed from fully hydrated particles.

In some circumstances, it is therefore advantageous to add an anti-freeze agent to the formulation, as it has been found that the presence of an anti-freeze agent results in products which stay as discrete particles when frozen, or form a block which is relatively easy to break down to the discrete particles. The main reasons for this effect appear to be: (1) the depression of the freezing point of the formulation, and (2) the inherent property of the polymer to absorb less water, and thus not to become fully hydrated, in the presence of an anti-freeze agent. Preferred anti-freeze agents include salts and glycol compounds. Preferably the salt is sodium chloride and the glycol is glycerol.

There is also a relationship between the concentration of the anti-freeze agent used and the ease with which a block of polymer, if formed, breaks down. It has been found that the ease with which the block can be broken down increases with increasing concentration of the anti-freeze agent.

The ease with which the frozen particles were broken down, and hence the conformability of the product, also depends on the polymer content in the formulation. Preferably, the polymer content is >10% w/w of the formulation.

The ease with which the frozen particles break down to become free flowing, and hence the conformability of the product, is also dependent on the amount of air present in the container. When there is sufficient air in the container for the discrete particles to flow freely at room temperature, when frozen the resulting product breaks down easily or flows freely. When the same formulation is used in a container from which the air has been expelled, e.g. using vacuum packing, then the product freezes into blocks which are relatively difficult to break down. However, it has been found that at higher polymer contents, i.e. >15% w/w, the polymer particles are more resilient, and even if a large lump of them is formed, it breaks down to the discrete particles relatively easily.

In the hot state the polymer particles do not change form at the temperatures of use, and remain as discrete free flowing particles. It should also be noted though that when the product is to be used as a hot compress it is preferable to exclude most of the air from the container, since the container may expand when the product is heated. Such an inflated product does not conform as well as a product which is not expanded. For example, it has been found that a product from which most of the air has been removed does not expand on heating and is as conformable as it was at room temperature or −18° C. It will therefore be appreciated that in some circumstances the final product developed will be a compromise between the various desired properties. For example, if a free flowing frozen product is required some air should preferably be left in the container, with the result that the heated container may expand slightly and not be at its optimum conformability when used as a hot compress.

BRIEF DESCRIPTION OF THE FIGURES

Various preferred features and embodiments of the present invention will now be described by way of non-limiting example with reference to the accompanying drawings, in which.

DETAILED DESCRIPTION OF THE INVENTION

Figure 1:
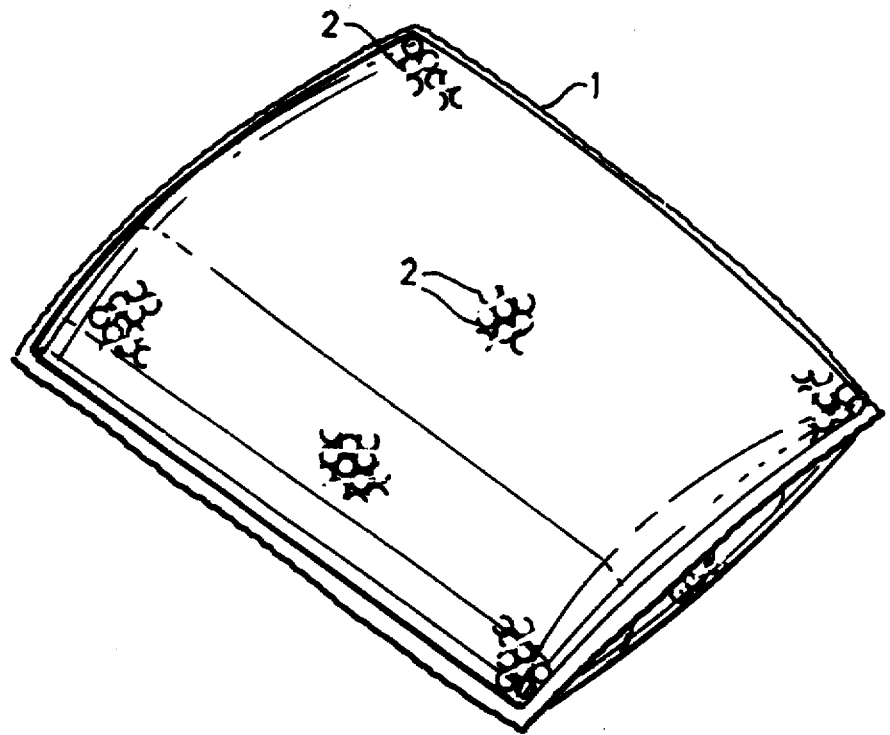
FIG. 1 shows a compress in accordance with an embodiment of the present invention.

As shown in FIG. 1, the compress takes the form of a flexible container (1) containing an aqueous solution and a crosslinked, hydratable polymer (2). The container should have good barrier properties against moisture and be stable at its temperatures of use, more specifically it should be flexible at temperatures down to −18° C. and be stable between −20° C. and 80° C. Even more preferably, the container should be puncture resistant at its temperatures of use; be suitable for microwaving; be soft to the touch; be clear; and not be affected by an anti-freeze agent.

A plastic bag can be conveniently used as the flexible container and has the advantage that its free end can be simply heat sealed after it has been filed with its aqueous solution and polymer contents. A preferred type of plastic bag is that used for "boil-in-the-bag" food products. Suitable plastic bags of LDPE (low density polyethylene), and particularly a nylon/PE composite, measure 15 by 25 cm and are commercially available from Moore and Buckle.

As previously mentioned, suitable polymers include ALCOSORB and SALSORB polymers. These polymers are available in a range of grades according to particle size. A particularly preferred polymer is ALCOSORB grade AB3C, where grade AB3C corresponds to a product in which 95% of the particles have a particle size within the 500 to 2800 micron range.

The aqueous solution is preferably in the form of water which is deionised.

As previously mentioned, any anti-freeze agent is preferably in the form of sodium chloride or glycerol. Both compounds are commercially available from various manufacturers.

Preferably, the contents are prepared by simply pouring the required amount of water into the container followed by the pre-weighted polymer. When an anti-freezing agent is also being used, the anti-freeze agent is mixed with the aqueous solution until homogeneous and then poured into the container. For general use as a cold and hot compress most of the air is expelled from the container whose open end is sealed with a heat sealer bar. The bag and its contents are preferably then allowed to stand at room temperature for at least 1 hour before use to enable the polymer to absorb the water.

For use as a compress for cold treatment, the compress can be used straight from a domestic freezer. A domestic freezer generally operates at a temperature of about −18° C., and it has been found that the compress should preferably be left in the freezer for about 6 hours. For use as a compress for hot treatment, the compress can conveniently be heated in a microwave oven or by placing it in boiling water for about 7 minutes, to reach a temperature of about 60° to 70° C.

For use, the hot or cold compress can be applied direct to the body, or it may be wrapped, e.g. in a towel, to decrease the cooling or heating rate of the part of the body to which it is applied. The compress is preferably placed in a pouch, which is preferably insulated on one side so that the compress remains effective for a longer period. Neoprene is a convenient insulation material. The compress can be strapped in place using, e.g. a bandage.

Preferably the polymers have some degree of crystallinity. The melting of a perfectly crystalline substance is an equilibrium process characterized by a marked volume change and a well-defined melting temperature. Polymers are never perfectly crystalline, but may contain crystallites of varying size. The use of a polymer which "crystallizes" will allow the cold compress to mimic the action of a bag of ice, or indeed a bag of frozen peas, i.e. the temperature of the compress will not rise until melting of the aqueous solution is complete.

Various preferred features of the present invention and its advantages will now be described in further detail in the following examples:

Various compress contents formulations were tested with regard to their conformability. A plastic bag of size 15×25 cm was used as the container. The results for compresses using SALSORB grade 90C, which has a mean particles size of from 100 to 850 micron and ALCOSORB grade AB3C are given in Tables 1 and 2 respectively.

TABLE 1

| Run | Salsorb 90C | | Water | | Properties after freezing |
|---|---|---|---|---|---|
| | % | g | % | g | |
| 1 | 11.0 | 44.0 | 89.0 | 356.0 | Breaks down but a few lumps |
| 2 | 10.0 | 40.0 | 90.0 | 360.0 | Breaks down into large lumps |
| 3 | 9.0 | 36.0 | 91.0 | 364.0 | Breaks down into large lumps |
| 4 | 8.0 | 32.0 | 92.0 | 368.0 | Not easy to break down |
| 5 | 7.0 | 28.0 | 93.0 | 372.0 | Not easy to break down |

TABLE 2

| Run | Alcosorb AB3C | | Water | | Properties after freezing |
|---|---|---|---|---|---|
| | % | g | % | g | |
| 1 | 11.00 | 44.0 | 89.0 | 356.0 | Breaks down easily |
| 2 | 10.0 | 40.0 | 90.0 | 360.0 | Breaks down easily but a few lumps |
| 3 | 9.0 | 36.0 | 91.0 | 364.0 | Breaks down easily |
| 4 | 8.0 | 32.0 | 92.0 | 368.0 | Breaks down easily |
| 5 | 7.0 | 28.0 | 93.0 | 372.0 | Breaks down easily |

For the tests of Table 2 a lot of air was left in the bags so that the polymer particles were free flowing at room temperature.

The tests of Table 2 were re-run with all the air expelled from the bags. All the frozen products then had to be broken down, and Run 1 was the easiest and Run 5 the most difficult to break down.

This test indicates that it is preferable to use Alcosorb rather than Salsorb due to Alcosorb's larger particle size (Alcosorb 500–2800 micron; Salsorb 100–850 micron). The use of smaller polymer particles has the effect of increasing the surface area of contact between the particles, and hence it becomes more difficult to break a frozen polymer block down to free flowing particles.

The formulations based on Alcosorb were re-tested for conformability in the presence of varying amounts of glycerol as an anti-freeze agent. The results are given in Table 3.

TABLE 3

| RUN NO. | ALCOSORB AB3C | | GLYCEROL BP | | WATER | | PROPERTIES AFTER FREEZING |
|---|---|---|---|---|---|---|---|
| | % | G | % | G | % | G | |
| 1 | 9.0 | 36.0 | 0.0 | 0.0 | 91.0 | 364.0 | DNBD |
| 2 | 9.0 | 36.0 | 5.0 | 20.0 | 86.0 | 344.0 | BDWD |
| 3 | 9.0 | 36.0 | 10.0 | 40.0 | 81.0 | 324.0 | BDFE |
| 4 | 9.0 | 36.0 | 15.0 | 60.0 | 76.0 | 304.0 | BDE |
| 5 | 10.0 | 40.0 | 0.0 | 0.0 | 91.0 | 360.0 | BDWD |
| 6 | 10.0 | 40.0 | 5.0 | 20.0 | 86.0 | 340.0 | BDFE |
| 7 | 10.0 | 40.0 | 10.0 | 40.0 | 81.0 | 320.0 | BDFE |
| 8 | 10.0 | 40.0 | 15.0 | 60.0 | 76.0 | 300.0 | BDE |
| 9 | 11.0 | 44.0 | 0.0 | 0.0 | 91.0 | 356.0 | BDWD |
| 10 | 11.0 | 44.0 | 5.0 | 20.0 | 86.0 | 336.0 | BDFE |
| 11 | 11.0 | 44.0 | 10.0 | 40.0 | 81.0 | 316.0 | BDE |
| 12 | 11.0 | 44.0 | 15.0 | 60.0 | 76.0 | 296.0 | BDE |
| 13 | 12.0 | 48.0 | 0.0 | 0.0 | 91.0 | 352.0 | BDFE |
| 14 | 12.0 | 48.0 | 5.0 | 20.0 | 86.0 | 332.0 | BDFE |
| 15 | 12.0 | 48.0 | 10.0 | 40.0 | 81.0 | 312.0 | BDE |
| 16 | 12.0 | 48.0 | 15.0 | 60.0 | 78.0 | 292.0 | BDE |

NOTES:
A Most of the air was expelled from the bags.
B DNBD does not break down
BDWD breaks down with difficulty
BDFE breaks down fairly easily
BDE breaks down easily It can be seen from the results in Table 3 that as the amount of glycerol is increased for the same concentration of polymer, the conformability of the compress increases. The results further indicate that the addition of an anti-freeze agent also gives a product which has an acceptable conformability even with a lower polymer concentration.

A similar test was performed using sodium chloride as the anti-freeze agent. The results are set out in Table 4.

TABLE 4

| RUN NO. | ALCOSORB AB3C | | 10% SALINE SOLUTION | | TOTAL | PROPERTIES AFTER FREEZING |
|---|---|---|---|---|---|---|
| | % | G | % | G | G | |
| 1 | 6.0 | 12.0 | 94.0 | 188.0 | 200.0 | DNBD |
| 2 | 8.0 | 16.0 | 92.0 | 184.0 | 200.0 | BDWD |
| 3 | 10.0 | 20.0 | 90.0 | 180.0 | 200.0 | BDFE |
| 4 | 12.0 | 24.0 | 88.0 | 176.0 | 200.0 | BDE |

Runs 5–7 were prepared and placed into bags same size as for runs 1–4 (ie. particles squashed together).

| 5 | 6.0 | 30.0 | 94.0 | 470.0 | 500.0 | DNBD |
| 6 | 8.0 | 40.0 | 92.0 | 460.0 | 500.0 | BDWD |
| 7 | 10.0 | 50.0 | 90.0 | 450.0 | 500.0 | BDWD |

The results confirm that as the amount of anti-freeze agent is increased for the same concentration of polymer, the conformability of the compress increases. The results also show that for cold compresses for optimum conformability, the polymer particles should not be compresses together prior to freezing, but should be free flowing.

Figure 2:
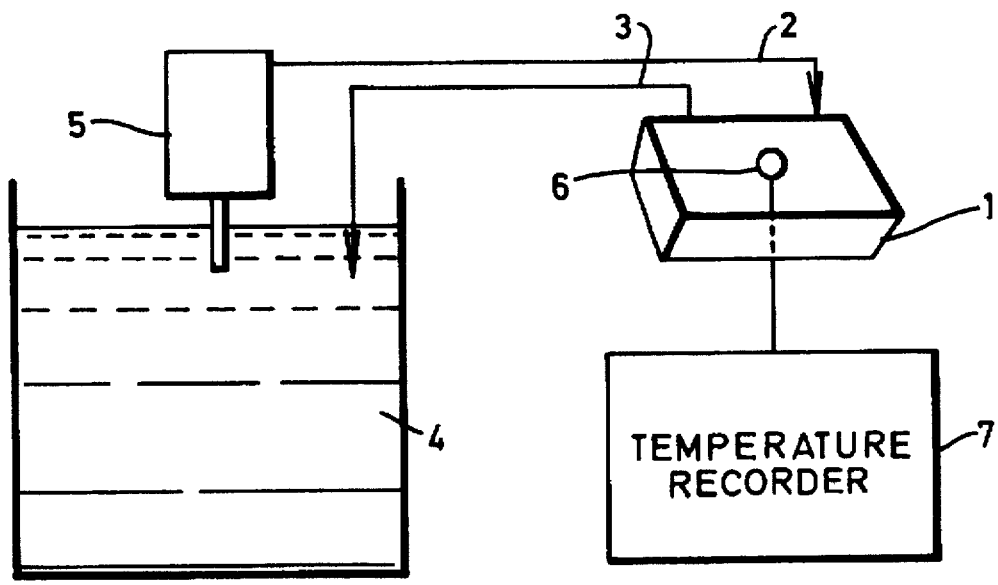
FIG. 2 shows the equipment used for monitoring the rate of heat transfer occurring in a compress.

Various compress formulations were also tested for their heat transfer rate using the equipment shown in FIG. 2. Referring to this FIG. 2, the compress under test is placed onto a hollow brass box having a water inlet 2 and outlet 3. The brass box is kept at a constant temperature by circulating water through it via a constant temperature water bath 4 using a pump 5. The brass box also contains a thermocouple 6 to measure the rate of heat transfer which is displayed on the recorder 7. The brass box was maintained at a temperature of 35°+/–0.1° C. and the temperature between the product and the brass box surface was monitored over a period of time. The results were then plotted to give graphs of temperature (° C.) v time (minute).

Figure 3:
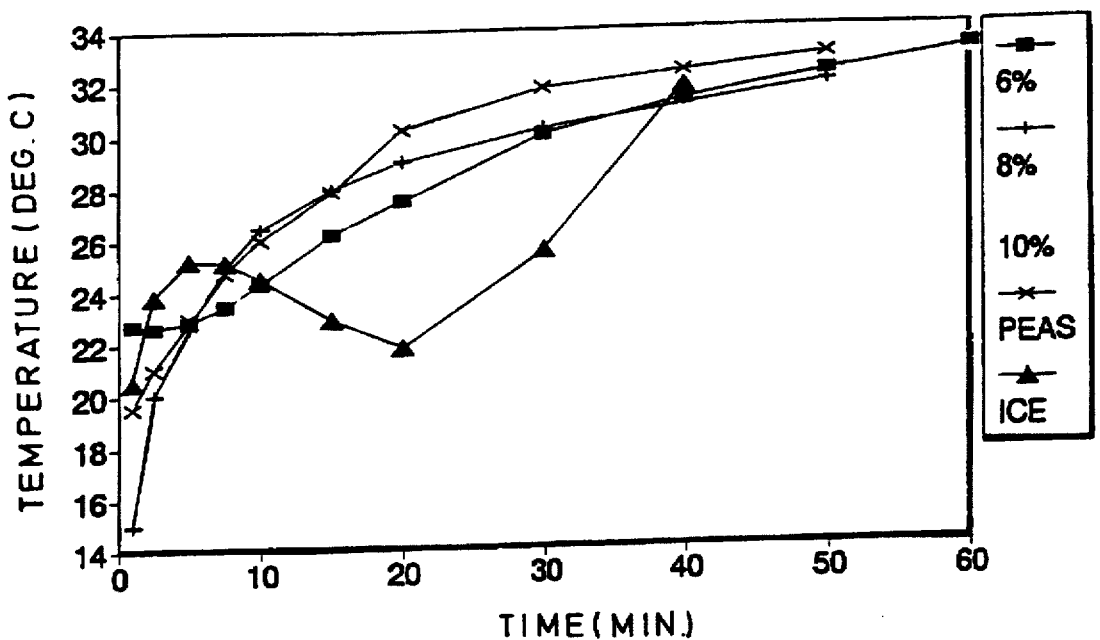
FIG. 3 is a graph showing the heat transfer rate profile of various cold compress formulations in accordance with embodiments of the present invention based on polymer, water and sodium chloride compared with bags of ice and frozen peas.

Initially the heat transfer rate of the cold compresses based on polymer, sodium chloride and water were compared with bags of ice and of frozen peas. The results are shown in Table 5 below which are plotted in the graph shown in FIG. 3 [the line for 10% is not plotted, but it will be very similar to the 8% plot].

TABLE 5

Alcosorb AB3C in 10% saline

| TIME, | TEMPERATURE (°C.) | | | | |
|---|---|---|---|---|---|
| | % w/w AB3c POLYMER | | | CONTROLS | |
| (MIN) | 6 | 8 | 10 | PEA | ICE |
| 1 | 22.7 | 15 | 17.7 | 19.5 | 20.5 |
| 2.5 | 22.6 | 20 | 20.5 | 21 | 23.8 |
| 5 | 22.3 | 22.6 | 24.8 | 23 | 25.2 |
| 7.5 | 23.4 | 24.9 | 25 | 24.7 | 25.1 |
| 10 | 24.3 | 26.4 | 26.5 | 26 | 24.5 |
| 15 | 26.2 | 28 | 27.2 | 27.9 | 22.9 |
| 20 | 27.5 | 29 | 28.2 | 30.2 | 21.8 |
| 30 | 30 | 30.2 | 29.6 | 31.7 | 25.5 |
| 40 | 31.2 | 31 | 30.8 | 32.3 | 31.7 |
| 50 | 32.2 | 31.8 | 32 | 32.9 | — |
| 60 | 33.1 | — | 32.9 | — | — |

The results show that the cooling rate profile of a frozen bag of peas could be matched with all the formulations tested. However, as previously mentioned, for reasons of conformability, an especially preferred product will have a higher polymer content and at least some air in the bag.

Figure 4:
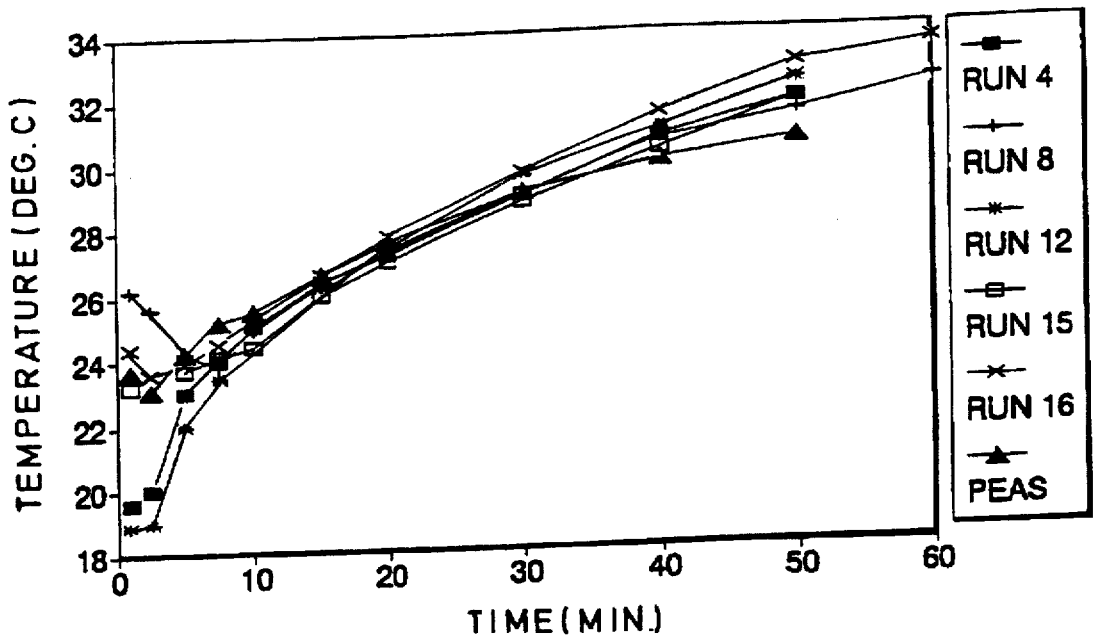
FIG. 4 is a graph showing the heat transfer rates of further cold compresses in accordance with embodiments of the present invention based on polymer, water and glycerol compared with a bag of frozen peas.

The heat transfer rate profiles for cold compresses based on polymer, glycerol and water were also tested, and compared to a bag of frozen peas, after 48 hours in a freezer at about –18° C. These results are shown in Table 6 the corresponding graph shown in FIG. 4. The formulations used in this test correspond to the formulations given in Table 3.

TABLE 6

| TIME, | TEMPERATURE (°C.) | | | | | |
|---|---|---|---|---|---|---|
| (MIN) | RUN 4 | RUN 8 | RUN 12 | RUN 15 | RUN 16 | PEAS |
| 1 | 19.6 | 26.2 | 18.9 | 23.2 | 24.4 | 23.7 |
| 2.5 | 20 | 25.6 | 19 | — | 23.6 | 23.1 |
| 5 | 23 | 24.2 | 22 | 23.7 | 23.9 | 24.2 |
| 7.5 | 24 | 23.8 | 23.4 | 24.1 | 24.5 | 25.2 |
| 10 | 25 | 24.9 | 24.2 | 24.4 | 25.3 | 25.5 |
| 15 | 26.4 | 26.4 | 26.1 | 26 | 26.6 | 26.6 |
| 20 | 27.2 | 27.3 | 27.4 | 27 | 27.8 | 27.6 |
| 30 | 29 | 29.1 | 29.6 | 28.8 | 29.7 | 29.1 |

TABLE 6-continued

| TIME, | TEMPERATURE (°C.) | | | | | |
|---|---|---|---|---|---|---|
| (MIN) | RUN 4 | RUN 8 | RUN 12 | RUN 15 | RUN 16 | PEAS |
| 40 | 30.7 | 30.6 | 31 | 30.3 | 31.4 | 30 |
| 50 | 31.8 | 31.4 | 32.4 | 31.8 | 32.9 | 30.6 |
| 60 | — | 32.3 | — | — | 33.5 | — |

Figure 5:
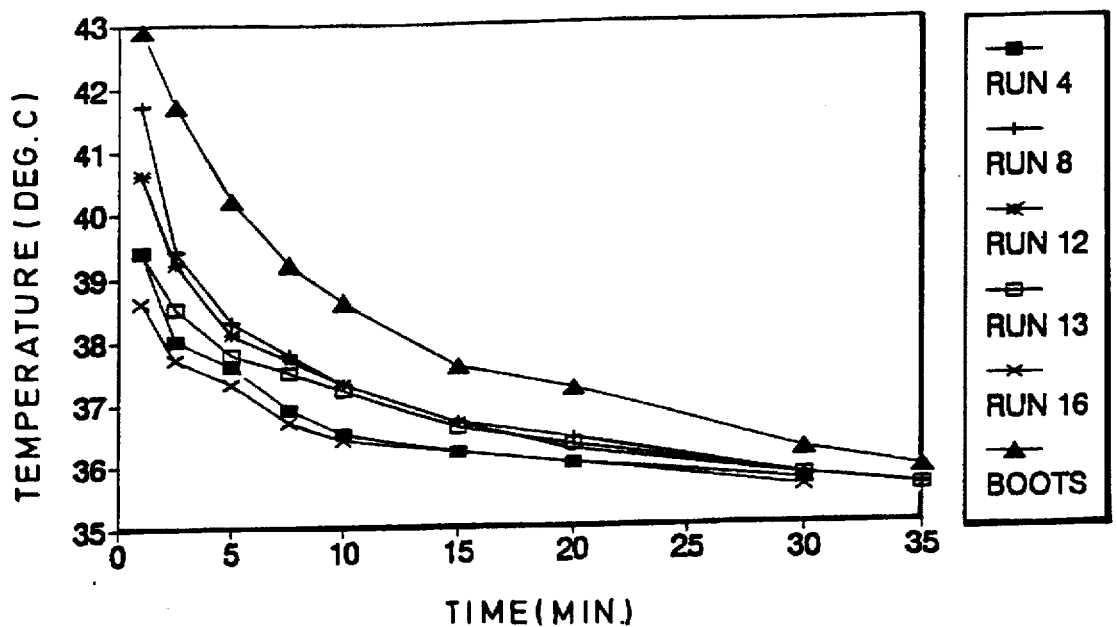
FIG. 5 is a graph showing the heat transfer rates of various hot compresses in accordance with embodiments of the present invention compared with a commercially available product.

The heat transfer rate profiles were then obtained for hot compresses based on Alcosorb AB3C polymer, glycerol and water. These compresses based on Alcosorb AB3C polymer, glycerol and water. These were compared with a commercially available compress called "Sports Hot/Cold Compress" available from the high street store "Boots The Chemists". Each of the products were tested after being heated for 1.5 minutes in a microwave on a setting of about 650 W. The results of this test are set out in Table 7 and plotted in the graph shown in FIG. 5.

TABLE 7

| TIME, | TEMPERATURE (°C.) | | | | | |
|---|---|---|---|---|---|---|
| (MIN) | RUN 4 | RUN 8 | RUN 12 | RUN 13 | RUN 16 | BOOTS |
| 1 | 39.4 | 41.7 | 40.6 | 39.4 | 38.6 | 42.9 |
| 2.5 | 38 | 39.4 | 39.2 | 38.5 | 37.7 | 41.7 |
| 5 | 37.6 | 38.3 | 38.1 | 37.8 | 37.3 | 40.2 |
| 7.5 | 36.9 | 37.8 | 37.7 | 37.5 | 36.7 | 39.2 |
| 10 | 36.5 | 37.3 | 37.3 | 37.2 | 36.4 | 38.6 |
| 15 | 36.2 | 36.7 | 36.7 | 36.6 | 36.2 | 37.6 |
| 20 | 36 | 36.4 | 36.2 | 36.3 | 36 | 37.2 |
| 30 | 35.7 | 35.5 | 35.8 | 35.8 | 35.6 | 36.2 |
| 35 | — | 35.6 | — | 35.6 | — | 35.9 |

Based on the above results the following preferred compress contents have been formulated:

| | % | g | % | g |
|---|---|---|---|---|
| | FORMULATION 34 | | FORMULATION 35 | |
| Alcosorb AB3C | 8.0 | 32 | 10.0 | 50.0 |
| Water | 73.6 | 368 | 72.0 | 360.0 |
| Glycerol | 18.4 | 92 | 18.0 | 90.0 |
| Sodium Chloride | — | — | — | — |
| | FORMULATION 36 | | FORMULATION 37 | |
| Alcosorb AB3C | 10.0 | 50 | 10.0 | 50.0 |
| Water | 67.5 | 337.5 | 72.0 | 360.0 |
| Glycerol | 22.5 | 112.5 | — | — |
| Sodium Chloride | — | — | 18.0 | 90.0 |

Figure 6:
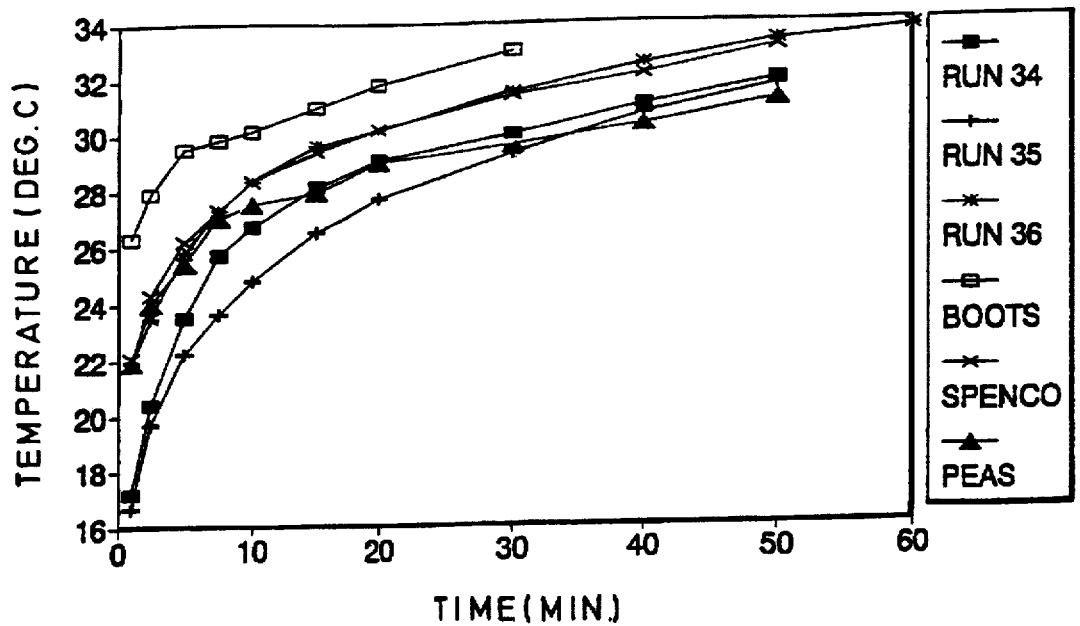
FIG. 6 is a graph showing the heat transfer rates of various preferred cold compress formulations in accordance with the present invention compared with various commercially available products and a bag of frozen peas.

The cooling rate profile results for these formulations are given in Table 8 and shown in the graph of FIG. 6. These results compare these preferred formulations with a bag of frozen peas, the commercially available product "Sports Hot/Cold Compress" from "Boots The Chemists", and a further commercially available product called "ThermaWrap" which is available from Spenco. The products are tested after spending 48 hours in a freezer at a temperature of about –18° C.

TABLE 8

| TIME, (MIN) | RUN 34 | RUN 35 | RUN 36 | BOOTS | SPENCO | PEAS | RUN 37 |
|---|---|---|---|---|---|---|---|
| 1 | 17.2 | 16.7 | 21.8 | 26.3 | 22.1 | 21.9 | 19.2 |
| 2.5 | 20.4 | 19.7 | 23.5 | 27.9 | 24.3 | 24.0 | 21.0 |
| 5 | 23.5 | 22.2 | 25.8 | 29.5 | 26.2 | 25.4 | 23.2 |
| 7.5 | 25.7 | 23.6 | 27.3 | 29.8 | 27.3 | 27.0 | 24.8 |
| 10 | 26.7 | 24.8 | 28.3 | 30.1 | 28.3 | 27.5 | 25.9 |
| 15 | 28.1 | 26.5 | 29.6 | 31.0 | 29.4 | 27.9 | 27.3 |
| 20 | 29.1 | 27.7 | 30.2 | 31.8 | 30.2 | 29.0 | 28.5 |
| 30 | 30.0 | 29.3 | 31.5 | 33.0 | 31.4 | 29.6 | 30.4 |
| 40 | 31.0 | 30.7 | 32.5 | — | 32.1 | 30.3 | 31.9 |
| 50 | 31.9 | 31.7 | 33.3 | — | 33.1 | 31.2 | 33.0 |
| 60 | — | — | 33.7 | — | — | — | — |

It will be seen that in Run 37 where the sodium chloride concentration is 18% w/w, the product does not freeze at all in a domestic freezer having a temperature of −18° C., and it therefore remains as flexible as it was at room temperature and has the same cooling curve as a bag of peas. When glycerol is present at 18% w/w as in Run 35, there is partial freezing of the product and even if a lump of polymer is produced, it breaks down very easily and therefore results in a very conformable product.

It is envisaged that other conventional additives, such as a dye to produce a coloured product, can be added to the formulation.

When used as a cold compress the compress is conveniently applied to the affected area for about 10–30 minutes, preferably followed by at least an equal non-treatment time. However, the precise time and method of application can be varied for each treatment and the details of each treatment will depend, among other things, on the initial temperature of the compress, and the patient's tolerance to cold.

It is recommended to start with a compress which is at a relatively high temperature and apply continually colder compresses as the treatment progresses. The affected area should be inspected before, during, and after treatment, for signs of cold injury. However, the product is suitable for self-application by the patient.

When used as a hot compress, the compress can again conveniently be applied to the affected for a period of 10–30 minutes. Again, for safety reasons, it is recommended that treatment starts with a relatively cool compress before progressing to higher temperatures, and the affected area should be inspected for the onset of any skin injury, such as a burn.

Another means of treatment would be to apply both cold and hot compresses to an affected area, e.g. alternatively. Preferably the ratio of application of cold to hot compress in such a form of treatment is about 1:1 to 4:1.

While various embodiments of the present invention have been described in detail, it is apparent that further modifications and adaptations of the invention will occur to those skilled in the art. However, it is to be expressly understood that such modifications and adaptations are within the spirit and scope of the present invention as set forth in the following claims.

What is claimed is:

1. A compress suitable for use in the cold and hot treatment of a part of a human or animal body comprising: a flexible container being impermeable to water containing a formulation comprising an aqueous solution, and discrete particles of a crosslinked, water-absorbing polymer, wherein all of said aqueous solution is absorbed by said discrete particles, and said discrete particles are partially hydrated and said container remaining flexible at temperatures down to −18° C.

2. A compress according to claim 1, wherein the crosslinked, water-absorbing polymer is polyacrylamide or a sodium polyacrylate.

3. A compress according to claim 1, wherein said flexible container is a sealed plastic bag.

4. A compress according to claim 1, wherein said particles have a particle size of between about 500 and about 2800 microns.

5. A method for treatment comprising:
   applying a compress in the cold and/or hot treatment of a part of a human or animal body, said compress comprising:
   a flexible container containing a formulation comprising an aqueous solution, and discrete particles of a crosslinked, water-absorbing polymer, wherein said aqueous solution is absorbed by said discrete particles, and the discrete particles are partially hydrated.

6. A compress suitable for use in the cold and hot treatment of a part of a human or animal body, comprising:
   a flexible container containing a formulation comprising an aqueous solution, and discrete particles of a crosslinked, water-absorbing polymer wherein said aqueous solution is absorbed by said discrete particles to partially hydrate said particles, said formulation further comprising an antifreeze agent comprising a salt compound, a glycol compound, or a mixture thereof.

7. A compress suitable for use in the cold and hot treatment of a part of a human or animal body, comprising:
   a flexible container containing a formulation comprising an aqueous solution, and discrete particles of a crosslinked, water-absorbing polymer, wherein said aqueous solution is absorbed by said discrete particles to partially hydrate said particles, said formulation further comprising an antifreeze agent comprising a salt compound, a glycol compound, or a mixture thereof, said salt compound comprising sodium chloride and said glycol compound comprising glycerol.

8. A compress suitable for use in the cold and hot treatment of a part of a human or animal body comprising: a flexible container containing a formulation comprising discrete particles of a crosslinked water absorbing polymer, and an amount of aqueous solution only sufficient to be fully absorbed by said discrete particles to render said discrete particles partially hydrated, said container remaining flexible at temperatures down to −18° C. such that said container is conformable to said body down to −18° C.

9. A compress suitable for use in the cold and hot treatment of a part of a human or animal body comprising: a flexible container containing a formulation comprising an aqueous solution, and discrete particles of a crosslinked, water-absorbing polymer, said aqueous solution being in an amount that is fully absorbed by said discrete particles so that said particles are partially hydrated, said container being impermeable against admission of further aqueous solution, said container remaining flexible at temperatures down to −18° C.

10. A compress suitable for use in the cold and hot treatment of a part of a human or animal body comprising: a flexible container containing a formulation comprising a given amount of aqueous solution, and discrete particles of a crosslinked, water-absorbing polymer, wherein all of said given amount of said aqueous solution is absorbed by said discrete particles and renders said particles partially hydrated, said container being impermeable against water from outside said container so that the partial hydration is achieved only with said given amount of said aqueous solution.

11. A compress suitable for use in the cold and hot treatment of a part of a human or animal comprising:

a flexible container containing a formulation comprising an aqueous solution, and discrete particles of a crosslinked, water-absorbing polymer, wherein said aqueous solution is absorbed by said discrete particles, and said discrete particles are partially hydrated, said formulation further comprising an anti-freeze agent comprising a salt compound, a glycol compound, or a mixture thereof.

12. A compress according to claim 11 wherein the salt compound is sodium chloride and the glycol compound is glycerol.

* * * * *